(12) United States Patent
Uberti et al.

(10) Patent No.: US 11,650,215 B2
(45) Date of Patent: May 16, 2023

(54) P53 PEPTIDES AS MARKERS IN THE DIAGNOSIS AND PROGNOSIS OF ALZHEIMER'S DISEASE

(71) Applicant: Diadem S.r.l., Brescia (IT)

(72) Inventors: Daniela Letizia Uberti, Brescia (IT); Maurizio Memo, Monticelli Brusati (IT)

(73) Assignee: Diadem S.r.l., Brescia (IT)

( * ) Notice: Subject to any disclaimer, the term of this patent is extended or adjusted under 35 U.S.C. 154(b) by 0 days.

(21) Appl. No.: 17/113,559

(22) Filed: Dec. 7, 2020

(65) Prior Publication Data

US 2021/0109116 A1    Apr. 15, 2021

Related U.S. Application Data

(63) Continuation of application No. PCT/IB2019/051785, filed on Mar. 6, 2019.

(51) Int. Cl.
*G01N 33/68* (2006.01)
(52) U.S. Cl.
CPC ............ *G01N 33/6896* (2013.01); *G01N 2800/2821* (2013.01); *G01N 2800/52* (2013.01)
(58) Field of Classification Search
CPC ....... G01N 33/6896; G01N 2800/2821; G01N 2800/52
See application file for complete search history.

(56) References Cited

U.S. PATENT DOCUMENTS

| 10,183,990 B2 * | 1/2019 | Memo | G01N 33/6896 |
| 10,875,908 B2 * | 12/2020 | Memo | G01N 33/6896 |
| 11,208,473 B2 * | 12/2021 | Memo | C07K 16/18 |
| 2019/0004038 A1 | 1/2019 | Lim et al. | |

FOREIGN PATENT DOCUMENTS

| KR | 20180073777 A | 7/2018 |
| WO | 2010037395 A2 | 4/2010 |
| WO | 2016050630 A1 | 4/2016 |

OTHER PUBLICATIONS

International Search Report and Written Opinion for International Application No. PCT/IB2019/051785, dated Nov. 22, 2019 (14 pages).
Arce-Varas N., et al. "Comparison of Extracellular and Intracellular Blood Compartments Highlights Redox Alterations in Alzheimer's and Mild Cognitive Impairment Patients." Current Alzheimer Research 2017; 14(1), pp. 112-122.
Buizza, L., et al., "Conformational Altered p53 as an Early Marker of Oxidative Stress in Alzheimer's Disease." PLoS one, 2012, 7(1), p. e29789.
Lanni, C., et al., "Homeodomain Interacting Protein Kinase 2: A Target for Alzheimer's Beta Amyloid Leading to Misfolded p53 and Inappropriate Cell Survival." PloS one, 2010, 5(4), p. e10171.
Lanni, C., et al., "Pharmacogenetics and Pharmagenomics, Trends in Normal and Pathological Aging Studies: Focus on p53." Current Pharmaceutical Design, 2008, 14(26), pp. 2665-2671.
Lanni, C., et al., "Unfolded p53: A Potential Biomarker for Alzheimer's Disease." In Journal of Alzheimer's Disease, 2007, pp. 93-99.
Lanni, C., et al., "Conformationally altered p53: a novel Alzheimer's disease marker?" Molecular Psychiatry, 2008, 13(6), pp. 641-647.
Lanni, C., et al., "Unfolded p53 in Blood as a Predictive Signature Signature of the Transition from Mild Cognitive Impairment to Alzheimer's Disease." Journal of Alzheimer's Disease, 2010, 20(1), pp. 97-104.
Stanga, S., et al., "Unfolded p53 in the pathogenesis of Alzheimer's disease: is HIPK2 the link?" Aging, 2010, 2(9), pp. 545-554.
Uberti, D., et al., "Conformationally Altered p53: A Putative Peripheral Marker for Alzheimer's Disease." Neuro-degenerative diseases, 2008, 5(3-4), pp. 209-211.
Uberti, D., et al., "Identification of a mutant-like conformation of p53 in fibroblasts from sporadic Alzheimer's disease patients." Neurobiology of Aging, 27(9), 2006, pp. 1193-1201.

* cited by examiner

*Primary Examiner* — Olga N Chernyshev

(74) *Attorney, Agent, or Firm* — Nutter McClennen & Fish LLP

(57) ABSTRACT

Disclosed are p53 peptides and their use as biomarkers in the diagnosis and/or prognosis of Alzheimer's disease (AD) in a biological sample. The invention also provides for a diagnostic method based on a highly accurate mass spectrometry analysis for the diagnosis of Alzheimer's disease at the pre-clinical and prodromal stages of the disease and for the prognosis of cognitive decline in a subject, by quantitating the levels of said p53 peptides specifically in human plasma of patients.

18 Claims, No Drawings
Specification includes a Sequence Listing.

```
                       SEQUENCE LISTING

<160> NUMBER OF SEQ ID NOS: 15

<210> SEQ ID NO 1
<211> LENGTH: 7
<212> TYPE: PRT
<213> ORGANISM: Homo sapiens

<400> SEQUENCE: 1

Thr Glu Glu Glu Asn Leu Arg
1               5

<210> SEQ ID NO 2
<211> LENGTH: 11
<212> TYPE: PRT
<213> ORGANISM: Homo sapiens

<400> SEQUENCE: 2

Thr Glu Glu Glu Asn Leu Arg Lys Gly Gly Lys
1               5                  10

<210> SEQ ID NO 3
<211> LENGTH: 14
<212> TYPE: PRT
<213> ORGANISM: Homo sapiens

<400> SEQUENCE: 3

Lys Lys Pro Leu Asp Gly Glu Tyr Phe Thr Leu Gln Ile Arg
1               5                  10

<210> SEQ ID NO 4
<211> LENGTH: 13
<212> TYPE: PRT
<213> ORGANISM: Homo sapiens

<400> SEQUENCE: 4

Glu Pro Gly Gly Ser Arg Ala His Ser Ser His Leu Lys
1               5                  10

<210> SEQ ID NO 5
<211> LENGTH: 27
<212> TYPE: PRT
<213> ORGANISM: Homo sapiens

<400> SEQUENCE: 5

Gly Glu Pro His His Glu Leu Pro Pro Gly Ser Thr Lys Arg Ala Leu
1               5                  10                  15

Pro Asn Asn Thr Ser Ser Ser Pro Gln Pro Lys
            20                  25

<210> SEQ ID NO 6
<211> LENGTH: 572
<212> TYPE: PRT
<213> ORGANISM: Mouse

<400> SEQUENCE: 6

Glu Val Gln Leu Gln Gln Ser Gly Pro Glu Leu Val Lys Pro Gly Ala
1               5                  10                  15
```

```
Ser Val Lys Met Ser Cys Lys Ala Ser Gly Tyr Thr Phe Thr Ser Tyr
             20                  25                  30
Val Met His Trp Val Lys Gln Lys Pro Gly Gln Gly Leu Glu Trp Ile
         35                  40                  45
Gly Tyr Ile Asn Pro Tyr Asn Asp Gly Thr Lys Tyr Asn Glu Lys Phe
     50                  55                  60
Lys Gly Lys Ala Thr Leu Thr Ser Asp Lys Ser Ser Ser Thr Ala Tyr
 65                  70                  75                  80
Met Glu Leu Ser Ser Leu Thr Ser Glu Asp Ser Ala Val Tyr Tyr Cys
                 85                  90                  95
Ala Arg Gly Gly Tyr Tyr Ala Met Asp Tyr Trp Gly Gln Gly Thr Ser
             100                 105                 110
Val Thr Val Ser Ser Glu Ser Gln Ser Phe Pro Asn Val Phe Pro Leu
         115                 120                 125
Val Ser Cys Glu Ser Pro Leu Ser Asp Lys Asn Leu Val Ala Met Gly
     130                 135                 140
Cys Leu Ala Arg Asp Phe Leu Pro Ser Thr Ile Ser Phe Thr Trp Asn
145                 150                 155                 160
Tyr Gln Asn Asn Thr Glu Val Ile Gln Gly Ile Arg Thr Phe Pro Thr
                 165                 170                 175
Leu Arg Thr Gly Gly Lys Tyr Leu Ala Thr Ser Gln Val Leu Leu Ser
             180                 185                 190
Pro Lys Ser Ile Leu Glu Gly Ser Asp Glu Tyr Leu Val Cys Lys Ile
         195                 200                 205
His Tyr Gly Gly Lys Asn Arg Asp Leu His Val Pro Ile Pro Ala Val
     210                 215                 220
Ala Glu Met Asn Pro Asn Val Asn Val Phe Val Pro Pro Arg Asp Gly
225                 230                 235                 240
Phe Ser Gly Pro Ala Pro Arg Lys Ser Lys Leu Ile Cys Glu Ala Thr
                 245                 250                 255
Asn Phe Thr Pro Lys Pro Ile Thr Val Ser Trp Leu Lys Asp Gly Lys
             260                 265                 270
Leu Val Glu Ser Gly Phe Thr Thr Asp Pro Val Thr Ile Glu Asn Lys
         275                 280                 285
Gly Ser Thr Pro Gln Thr Tyr Lys Val Ile Ser Thr Leu Thr Ile Ser
     290                 295                 300
Glu Ile Asp Trp Leu Asn Leu Asn Val Tyr Thr Cys Arg Val Asp His
305                 310                 315                 320
Arg Gly Leu Thr Phe Leu Lys Asn Val Ser Ser Thr Cys Ala Ala Ser
                 325                 330                 335
Pro Ser Thr Asp Ile Leu Thr Phe Thr Ile Pro Pro Ser Phe Ala Asp
             340                 345                 350
Ile Phe Leu Ser Lys Ser Ala Asn Leu Thr Cys Leu Val Ser Asn Leu
         355                 360                 365
Ala Thr Tyr Glu Thr Leu Asn Ile Ser Trp Ala Ser Gln Ser Gly Glu
     370                 375                 380
Pro Leu Glu Thr Lys Ile Lys Ile Met Glu Ser His Pro Asn Gly Thr
385                 390                 395                 400
Phe Ser Ala Lys Gly Val Ala Ser Val Cys Val Glu Asp Trp Asn Asn
                 405                 410                 415
Arg Lys Glu Phe Val Cys Thr Val Thr His Arg Asp Leu Pro Ser Pro
             420                 425                 430
```

Gln Lys Lys Phe Ile Ser Lys Pro Asn Glu Val His Lys His Pro Pro
            435                 440                 445
Ala Val Tyr Leu Leu Pro Pro Ala Arg Glu Gln Leu Asn Leu Arg Glu
450                 455                 460
Ser Ala Thr Val Thr Cys Leu Val Lys Gly Phe Ser Pro Ala Asp Ile
465                 470                 475                 480
Ser Val Gln Trp Leu Gln Arg Gly Gln Leu Leu Pro Gln Glu Lys Tyr
                485                 490                 495
Val Thr Ser Ala Pro Met Pro Glu Pro Gly Ala Pro Gly Phe Tyr Phe
            500                 505                 510
Thr His Ser Ile Leu Thr Val Thr Glu Glu Glu Trp Asn Ser Gly Glu
        515                 520                 525
Thr Tyr Thr Cys Val Val Gly His Glu Ala Leu Pro His Leu Val Thr
    530                 535                 540
Glu Arg Thr Val Asp Lys Ser Thr Gly Lys Pro Thr Leu Tyr Asn Val
545                 550                 555                 560
Ser Leu Ile Met Ser Asp Thr Gly Gly Thr Cys Tyr
                565                 570

<210> SEQ ID NO 7
<211> LENGTH: 214
<212> TYPE: PRT
<213> ORGANISM: Mouse

<400> SEQUENCE: 7

Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asn Thr Leu Pro Tyr
                85                  90                  95
Thr Phe Gly Gly Gly Thr Lys Leu Glu Ile Lys Arg Ala Asp Ala Ala
            100                 105                 110
Pro Thr Val Ser Ile Phe Pro Pro Ser Ser Glu Gln Leu Thr Ser Gly
        115                 120                 125
Gly Ala Ser Val Val Cys Phe Leu Asn Asn Phe Tyr Pro Lys Asp Ile
    130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

-continued

```
<210> SEQ ID NO 8
<211> LENGTH: 117
<212> TYPE: PRT
<213> ORGANISM: Mouse

<400> SEQUENCE: 8

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Gly Tyr Tyr Ala Met Asp Tyr Trp Gly Gln Gly Thr Ser
            100                 105                 110

Val Thr Val Ser Ser
        115

<210> SEQ ID NO 9
<211> LENGTH: 107
<212> TYPE: PRT
<213> ORGANISM: Mouse

<400> SEQUENCE: 9

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 10
<211> LENGTH: 5
<212> TYPE: PRT
<213> ORGANISM: Mouse

<400> SEQUENCE: 10

Ser Tyr Val Met His
1               5

<210> SEQ ID NO 11
<211> LENGTH: 17
<212> TYPE: PRT
<213> ORGANISM: Mouse
```

```
<400> SEQUENCE: 11

Tyr Ile Asn Pro Tyr Asn Asp Gly Thr Lys Tyr Asn Glu Lys Phe Lys
1               5                   10                  15
Gly

<210> SEQ ID NO 12
<211> LENGTH: 8
<212> TYPE: PRT
<213> ORGANISM: Mouse

<400> SEQUENCE: 12

Gly Gly Tyr Tyr Ala Met Asp Tyr
1               5

<210> SEQ ID NO 13
<211> LENGTH: 11
<212> TYPE: PRT
<213> ORGANISM: Mouse

<400> SEQUENCE: 13

Arg Ala Ser Gln Asp Ile Ser Asn Tyr Leu Asn
1               5                   10

<210> SEQ ID NO 14
<211> LENGTH: 7
<212> TYPE: PRT
<213> ORGANISM: Mouse

<400> SEQUENCE: 14

Tyr Thr Ser Arg Leu His Ser
1               5

<210> SEQ ID NO 15
<211> LENGTH: 9
<212> TYPE: PRT
<213> ORGANISM: Mouse

<400> SEQUENCE: 15

Gln Gln Gly Asn Thr Leu Pro Tyr Thr
1               5
```

P53 PEPTIDES AS MARKERS IN THE DIAGNOSIS AND PROGNOSIS OF ALZHEIMER'S DISEASE

CROSS-REFERENCE TO RELATED APPLICATIONS

This application is a U.S. national stage application of PCT/IB2019/051785, filed Mar. 6, 2019.

SEQUENCE LISTING

This application contains a Sequence Listing which has been submitted electronically in ASCII format and is hereby incorporated by reference in its entirety. Said ASCII copy, created on Sep. 28, 2021, is named 121689-10201_Sequence_Listing_09-28-2021_ST25.txt and is 11 kilobytes in size.

FIELD OF THE INVENTION

The present invention refers to p53 peptides P1, P2, P3 and P5 and to their use as biomarkers in the diagnosis and/or prognosis of Alzheimer's disease (AD) in a biological sample. The invention also provides for a diagnostic method based on a highly accurate mass spectrometry analysis for the diagnosis of Alzheimer's disease at the pre-clinical and prodromal stages of the disease and for the prognosis of cognitive decline in a subject, by quantitating the levels of said p53 peptides specifically in human plasma of patients.

BACKGROUND ART

The confirmation of the presence of a large amount of altered conformational p53 isoform as an early risk factor for Alzheimer's disease (shortly 'AD') have been demonstrated in different published studies [1-3]. Initially, more than 400 subjects among AD, Mild Cognitive Impairment, Parkinson Disease, other Dementia and healthy subjects were enrolled in different independent studies and tested for Unfolded p53 by using different techniques (immunoprecipitation experiments, FACS analysis, ELISA) with a commercial conformational specific anti-p53 antibody [4-7]. In 2006 for the first time Uberti et al. [8], demonstrated that fibroblasts from sporadic Alzheimer's disease (AD) patients specifically expressed an anomalous and detectable conformational state of p53 that differentiate these cells from fibroblasts of age-matched non-AD subjects. In this conformational altered state, p53 lost its ability to transactivate its target genes, and consequently its biological functions [9-10]. The higher amount of unfolded p53 was also confirmed in blood of AD compared to healthy-non demented subjects or patients affected by other dementia and PD, as well as in MCI converted to AD.

Altogether these data suggested a direct association between Unfolded p53 and AD pathology.

In EP3201234B1, it has been reported the development of a new conformational specific anti-Up53 antibody named 2D3A8, that binds to an epitope (aa 282-297), accessible only when p53 loses its wild type conformation towards an unfolded phenotype. Comparing to the commercial antibody used at the beginning of Unfolded p53 discovering in AD (PAb240, aa214-217), the 2D3A8 antibody showed higher sensitivity and specificity in identifying AD patients compared to healthy elderly in Oviedo cohort.

In particular, said immunodiagnostic method is able to identify immunocomplex in a biological sample that are indicative of AD and to determine the predisposition of a subject affected by Mild Cognitive Impairment (MCI) to develop AD.

There is now the need of identifying new specific biological markers that can be used in the diagnosis and/or prognosis of Alzheimer's disease and of developing an accurate and sensible diagnostic method that can be used for the diagnosis and/or prognosis of AD, in particular at the pre-clinical and prodromal stages of the disease and for the differential analysis of AD from other forms of dementia.

SUMMARY OF THE INVENTION

This object has been achieved by identifying four p53 peptides, called P1 (SEQ ID N. 1), P2 (SEQ ID N. 2), P3 (SEQ ID N. 3) and P5 (SEQ ID N. 5) having the sequences reported in the claims, in a biological sample.

Another aspect of the present invention relates to a diagnostic method based on the identification and quantification of said peptides, for use in the diagnosis and/or in the prognosis of Alzheimer's disease at different stages.

The characteristics and the advantages of the present invention will become apparent from the following detailed description and the working examples provided for illustrative purposes.

DETAILED DESCRIPTION OF THE INVENTION

The invention therefore relates to a highly accurate mass spectrometry method for the diagnosis of Alzheimer's disease at the pre-clinical and prodromal stages of the disease. Said method is based on the identification and quantification of the levels of specific p53 peptides, shorty referred to as "P1", "P2", "P3", and "P5" or "p53 peptides", that have been detected by mass spectrometry analysis in human plasma of patients affected by Alzheimer's disease or patients that have symptoms that can predispose to the development of AD.

In particular, the mass spectrometry analysis is a qualitative and quantitative method that was performed when no information about the exact correlation between these specific sequences of p53 and AD was known.

First, p53 peptides, present in plasma of patients affected by AD, have been identified by deep sequencing protein method in plasma from patient at pre-clinical, prodromal clinical stages of Alzheimer's, MCI stable patients, and cognitive normal subjects. Then the levels of the p53 peptides have been quantitated in plasma with a highly sensitive selective reaction monitoring (SRM) mass spectrometry method carrying out an Area Under the ROC Curve (AUC) (where 'ROC Curve' means 'receiver operating characteristic curve').

The data obtained therefore demonstrate a strong evidence that the p53 peptides can be considered as biomarkers in the diagnosis and/or prognosis of AD.

Said method is advantageously fast, requires a small volume of plasma sample and quantifies the concentration of the p53 peptides in each sample analysed.

Furthermore, the method and the biomarkers identified can be used also in the diagnosis of Alzheimer's disease in asymptomatic individuals and people suffering from MCI, allowing the access to the diagnostics market.

In addition, since said biomarkers can be used in the prognosis of cognitive decline to Alzheimer's Dementia in asymptomatic and MCI subjects, said method allows the use of a p53 peptide expression to select the subjects in clinical trials to enable success of the trial and to differentiate patients affected by AD from other forms of dementia.

It is therefore an embodiment of the present invention a p53 peptide consisting of formula (I) P1: TEEENLR (SEQ ID N. 1). Alternatively, the p53 peptides of the present invention have an amino acid sequence with at least 80-90% of identity to the sequence of formula (I), preferably at least 90-95% of identity to the sequence of formula (I), more preferably at least 96-99% of identity to the sequence of formula (I).

A further embodiment of the present invention is a p53 peptide having formula (II) P2: TEEENLRK[GG]K (SEQ ID N. 2), where [GG] is a moiety of a residue tail of ubiquitin that derives from the ubiquitination at K291 of the p53 protein after post-translational modification. In this regard, for the purposes of the present invention, the term in square brackets "[GG]" denotes that the first-K amino acid of the P2 sequence is branched by said moiety.

An additional embodiment of the present invention is a p53 peptide consisting of formula (II) P2: TEEENLRK[GG]K (SEQ ID N. 2), where [GG] is as above defined. Alternatively, the p53 peptides of the present invention have an amino acid sequence with at least 80-90% of identity to the sequence of formula (II), preferably at least 90-95% of identity to the sequence of formula (II), more preferably at least 96-99% of identity to the sequence of formula (II).

A further embodiment is the use of the p53 peptides P1 and/or P2 according to the present invention as in vitro biomarker for the diagnosis and/or prognosis of Alzheimer's disease. A further embodiment of the present invention is a p53 peptide having formula (III) P3:

KKPLDGEYFTLQIR (SEQ ID N. 3)

An additional embodiment of the present invention is a p53 peptide consisting of formula (III) P3:

KKPLDGEYFTLQIR (SEQ ID N. 3)

A further embodiment of the present invention is a p53 peptide having formula (V) P5:

GEPHHELPPGSTKRALPNNTSSSPQPK (SEQ ID N. 5)

An additional embodiment of the present invention is a p53 peptide consisting of (V) P5:

GEPHHELPPGSTKRALPNNTSSSPQPK (SEQ ID N. 5)

A further embodiment is the use of the p53 peptides P3 and/or P5 according to the present invention as in vitro biomarker for the diagnosis of Alzheimer's disease.

A further embodiment of the present invention is an in vitro or ex vivo method for the diagnosis and/or prognosis of Alzheimer's disease, the method comprising the steps of:
a) determining the presence of a p53 peptide in a biological sample, and
b) quantifying said peptide by comparing the same with a given internal control.

In a preferred embodiment, the p53 peptide in step a) is the p53 peptide P1 or P2.

In a preferred embodiment, the method of the present invention also comprises a step c) of correlating the quantity of the p53 peptide with the diagnosis of Alzheimer's disease in a patient at different stages of the diseases.

Preferably, said biological sample is blood, plasma, serum, saliva, urine, neuronal cells, blood cells or other types of cells.

In a preferred embodiment, in the method according to the present invention, the step a) is performed by immunoprecipitating the p53 peptide with a monoclonal antibody that binds to a p53 peptide.

Preferably, said monoclonal antibody is the antibody 2D3A8. The amino acid sequences of the 2D3A8 antibody include the heavy chain (SEQ ID NO: 6) and light chain (SEQ ID NO: 7), heavy chain variable region (SEQ ID NO: 8) and light chain variable region (SEQ ID NO: 9), heavy chain CDRs 1, 2 and 3 (SEQ ID NOS: 10, 11 and 12, respectively) and light chain CDRs 1, 2 and 3 (SEQ ID NOS: 13, 14 and 15, respectively) In a preferred embodiment in the method according to the present invention the step b) is performed through mass spectrometry analysis, preferably by HPLC-mass spectrometry.

In a further preferred embodiment in step b) labelled peptides are used as internal controls. According to a preferred embodiment the in vitro or ex vivo method of the present invention comprises the following steps:
a) determining the presence of the p53 peptide in a biological sample, by:
  (i) providing a biological sample;
  (ii) performing protein immunoprecipitation by an antibody that binds a p53 peptide;
  (iii) performing protein fragmentation by trypsin;
  (iv) performing Strong Cation Exchange Chromatography of the peptides;
and
b) quantifying said p53 peptide by comparing the same with a given internal control, by:
  (v) performing a Selected Reaction Monitoring analysis to identify and quantify the p53 peptide by comparing it with a given control.

Preferably, the antibody of step a) (ii) is 2D3A8.

Preferably, the biological sample of step a)(i) is subjected to protein plasma depletion by HPLC or chromatographic columns, before performing step a)(ii).

According to a preferred embodiment the in vitro or ex vivo method of the present invention is used for the diagnosis of Alzheimer's disease in asymptomatic individuals and people suffering from MCI.

Preferably, in asymptomatic individuals and people suffering from MCI, the quantity of the p53 peptide is of 0.05 fmol/40 µl to 6.70 fmol/40 µl.

According to a further preferred embodiment, the in vitro or ex vivo method of the present invention is used for the prognosis of cognitive decline of Alzheimer's disease in asymptomatic individuals and people suffering from MCI.

Preferably, in asymptomatic and MCI subjects that have the prognosis of cognitive decline of Alzheimer's dementia, the quantity of the p53 peptide is of 0.203 fmol/40 µl to 6.70 fmol/40 µl.

Preferably, in asymptomatic individuals, the AUC is at least 80%.

Preferably, in people suffering from MCI, the AUC is at least 90%.

Measures of accuracy of a diagnostic/prognostic method include sensitivity and specificity. Sensitivity is the probability of a positive test result among those having the target condition, and it is measured by the formula:

Sensitivity=true positives/(true positive+false negative). Specificity is the probability of a negative test result among those without the target condition, and it is measured by the formula: Specificity=true negatives/(true negative+false positives).

Preferably, in asymptomatic individuals, the sensitivity of the p53 peptide is at least 70%.

Preferably, in people suffering from MCI, the sensitivity of the p53 peptide is at least 90%.

Preferably, in asymptomatic individuals, the specificity of the p53 peptide is at least 90%.

Preferably, in people suffering from MCI, the specificity of the p53 peptide is at least 90%.

In a further preferred embodiment, the in vitro or ex vivo method of the present invention is used for the differential analysis of Alzheimer's disease from other dementia, said other dementia being selected from fronto temporal dementia (FTD), Lewi's Body, Parkinson's disease and vascular dementia.

Preferably, in patients affected by Alzheimer's disease, the quantity of said p53 peptide is of 2.21 fmol/40 µl to 6.56 fmol/40 µl, while in patients affected by other forms of dementia the quantity of said p53 is lower than 3.81 fmol/40 µl.

Preferably, in patients affected by Alzheimer's disease, the AUC is at least 85%.

Preferably, in patients affected by Alzheimer's disease, the sensitivity of the p53 peptide is at least 75%.

Preferably, in patients affected by Alzheimer's disease, the specificity of the p53 peptide is at least 80%.

A further embodiment of the present invention is a method of detecting a p53 peptide as above described, said method comprising the following steps:
a) determining the presence of the p53 peptide in a biological sample, and
b) quantifying said peptide by comparing the same with a given control.

In a further preferred embodiment, the method of the present invention further comprising a step c) of correlating the quantity of the p53 peptide with the diagnosis and/or prognosis of Alzheimer's disease.

According to a preferred embodiment, in the method of the present invention, step c) correlates the quantity of the p53 peptide with the diagnosis of Alzheimer's disease in asymptomatic individuals and people suffering from MCI.

In a preferred embodiment, the p53 peptide in step a) is the p53 peptide P1 or P2.

According to a further embodiment, in the method of the present invention, in step c) the quantity of the p53 peptide is correlated with the prognosis of cognitive decline of Alzheimer's disease in asymptomatic individuals and people suffering from MCI.

More preferably, in the method of the present invention, in step c) the quantity of the p53 peptide is correlated with the differential analysis of Alzheimer's disease from other dementia, said other dementia being selected from fronto temporal dementia (FTD), Lewi's Body, Parkinson's disease and vascular dementia.

It should be also understood that all the combinations of preferred aspects of the peptides of the invention, as well as of the preparation processes, and methods using of the same, as above reported, are to be deemed as hereby disclosed.

All combinations of the preferred aspects of the peptides of the invention, preparation processes, and methods disclosed above are to be understood as herein described. Below are working examples of the present invention provided for illustrative purposes.

Examples

Materials and Methods
Materials

Antibody-based plasma/serum depletion Seppro® IgY14 LC10 column was purchased from Sigma-Aldrich (Merck KGaA, Darmstadt, Germany). Trypsin (Sequencing grade modified porcine) was obtained from Promega. Acetonitrile was purchased from JT Baker, and formic acid was obtained from EMD Millipore (Billerica, Mass., USA). C18 Cartridges for sample preparation, and chromatography columns for bRPLC and online HPLC of Triple Quadrupole mass spectrometer were purchased from Waters (Milford, Mass.). Plasma Dilution Buffer, -PlasmaWashing Buffer and -Plasma Elution Buffer, were prepared following standard protocols for this method. All other reagents were purchased from Sigma-Aldrich (St. Louis, Mo.) unless otherwise indicated.

Plasma Sample Depletion

The most abundant proteins in the plasma were depleted using a Seppro IgY14 column. Plasma samples were diluted 5× in Plasma Dilution buffer, filtered (0.22 m), then injected into IgY LC10 columns attached to an Agilent 1200 HPLC system. The unretained fraction was collected. High-abundance proteins were eluted Plasma Elution buffer.

Immunoprecipitation (IP)

Antibody clone 2D3A8 was used in the IP reactions. Conjugation of antibodies to beads was optimized and performed using with Link buffers. The monoclonal antibody was added directly to Protein G Dynal Magnetic Beads (as obtained from Invitrogen), and the antibody was bound to the beads in a buffer on a rotator at room temperature for 2 h. The antibody-bound beads then were washed by incubation in 50 mL Link-A buffer and collected on a magnet. The antibody was cross-linked to the protein G on the beads by incubation with 50 mL B buffer on a rotator at room temperature for 1 h. The beads then were washed twice with 50 mL C buffer, resuspended in 50 mL C buffer, and rotated at room temperature for 15 min. The beads were resuspended in C buffer and were stored at −20° C. until application. 200 µl depleted or undepleted plasma samples were used for IP reactions, each sample is reconstituted with IP buffer into a 3 ml system and 3 ml antibody conjugated beads (1:1 volume ratio) were added to the system. The IP systems were incubated on a rotator with a speed of 32 rounds per minute at 4° C. for 18 hours. Beads were collected on a magnet and washed by IP-Wash buffer at 4° C. for 3 times, followed by elution of the antigen through IP-Elution buffer. Flow-through fractions were collected for protein sample preparation.

Protein Preparation

Protein samples were processed in compliance with "Filter Assisted Sample Preparation" (FASP) method (Nat Methods. 2009, 6:359-362). Briefly, protein samples in 9M UREA were reduced with 5 mM TCEP at 37° C. for 45 min and reduced cysteines were blocked using 50 mM iodoacetamide at 25° C. for 15 min. Protein samples (100 µg each) were then cleaned using 10 kDa Amicon Filter (UFC501096, Millipore) three times using 9M urea and two times using Buffer 1. Samples were then proteolyzed with trypsin (V5111, Promega) for 12 hrs at 37° C. The peptide solution then was acidified by adding 1% trifluoroacetic acid (TFA) and was incubated at room temperature for 15 min. A Sep-Pak light C18 cartridge (Waters Corporation) was activated by loading 5 mL 100% (vol/vol) acetonitrile and was washed by 3.5 mL 0.1% TFA solution two times.

Acidified digested peptide solution was centrifuged at 1,800×g for 5 min, and the supernatant was loaded into the cartridge. To desalt the peptides bound to the cartridge, 1 mL, 3 mL, and 4 mL of 0.1% TFA were used sequentially. To elute the peptides from the cartridge, 2 mL of 40% (vol/vol) acetonitrile with 0.1% TFA was used, and this elution was repeated two more times (for a total of 6 mL of eluate). It was important to ensure that the cartridge had stopped dripping before each sequential wash and elution solution was applied. The eluted peptides were lyophilized overnight and reconstituted in 100 µL of Buffer 2.

Strong Cation Exchange Chromatography

Peptides were fractionated by strong cation exchange (SCX) chromatography. Briefly, lyophilized peptides mixture was resuspended in 1 ml of SCX solvent A (5 mM KH2PO4 pH 2.7, 30% ACN) and fractionated by SCX chromatography on a PolySULPHOETHYL A (5 m, 200 Å) column (200×9.4 mm; PolyLC Inc., Columbia, Md.) by employing an increasing gradient of SCX solvent B (5 mM KH2PO4 pH 2.7, 30% ACN, 350 mM KCl) on an Agilent 1290 Infinity II LC system. For each experiment, a total of 96 fractions were initially collected, which were then pooled into 24 fractions, and dried using SpeedVac (Eppendorf). bRPLC and SCX were performed side by side to compare the compatibility of detection of TP53 proteins, and SCX was chosen because a relative stronger yield of TP53 isoforms has been repeatedly observed for this project.

Optimization of Peptide SRM Transitions 4 peptides from targeting TP53 protein were chosen as SRM quantifying targets and 1092 sets of transition parameters and retention times of the 4 peptides were established individually using an Agilent 6495 Triple Quadrapole Mass Spectrometer for 1+, 2+, 3+ and 4+ charged precursor ions. 2 peptides (P1 and P2) were then selected as main correlated to the AD pathology.

Selected Reaction Monitoring (SRM) Analysis

Peptide samples reconstituted in 37 ul Buffer 3 were spiked with SRM Internal Control Mixture composed of a pool of 1 femto mole heavy isotope labeled peptides covering a large hydrophobicity window and a large M/z range (M/z 200~1300), Peptide samples were eluted through an online Agilent 1290 HPLC system into the Jet Stream ESI source of an Agilent 6495 Triple Quadrupole Mass spectrometer.

Results

There were cumulatively 5 peptides detected in previous projects for p53 protein in plasma [P1: TEEENLR (SEQ ID N. 1); P2: TEEENLRK[GG]K (SEQ ID N. 2), P3: KKPLDGEYFTLQIR (SEQ ID N. 3), P4: EPGGSRAHSSHLK (SEQ ID N. 4); and P5: GEPHHELPPGSTKRALPNNTSSSPQPK (SEQ ID N. 5)]. It was established the SRM detection method for 4 peptides. The peptide GEPHHELPPGSTKRALPNNTSSSPQPK (SEQ ID N. 5) is not feasible for SRM-based detection due to its high molecular weight.

Correlation Between p53 Sequence Peptide and AD Diagnosis.

Example 1. Detection of p53 Peptide Markers for Alzheimer's at the Asymptomatic (Cognitive Normal) and MCI Stages by Deep Sequencing Protein Method A deep sequence mass spectrometry analysis of human plasma immuno-precipitated was conducted with the conformationally specific Ab 2D3A8. Plasma sample was depleted from abundant proteins according to the method reported above. Samples were then immunoprecipitated by 2D3A8 and analyzed using Orbitrap (deep sequence mass spectrometry analysis). The resulting peptides present uniquely in AD, MCI to AD and asymptomatic to AD and absent in asymptomatic and MCI stable samples were chosen as markers. The detection of the peptide (presence/absence) by this method was correlated with clinical diagnosis of the subjects.

It was analyzed a pool of 10 samples from PiB (Pittsburgh compound B)+ve AD (PiB+ve) patients (AD), a pool of 10 baseline plasma samples from asymptomatic PiB negative individuals who remained both asymptomatic and PiB-ve for at least 108 months post baseline (Normal), a pool of 10 baseline plasma samples from PiB+ve patients with MCI 18 months before they converted to AD symptoms (Prodromal, MCI due to AD), a pool of 10 baseline plasma samples from PiB-ve patients with MCI who did not experience further cognitive decline to AD symptoms (follow up 18-72 months post baseline), (MCI stable) and 3 baseline plasma samples from PiB+ve patients with MCI 18 months before they converted to AD symptoms (Preclinical, Normal to AD converters).

TABLE 1

Inclusion Criteria for baseline characteristics

|  | Minimum age | f/m (minimum %) |
|---|---|---|
| Prodromal (MCI to AD) | 70 | 0.40 |
| Preclinical (Cognitive Normal to AD converters) | 70 | 0.4 |
| MCI stable | 70 | 0.40 |
| Cognitive Normal | 66 | 0.5 |
| Alzheimer's disease with dementia | 67 | 0.5 |

Results

TABLE 2

Validation of p53 marker performance in diagnosis of AD in asymptomatic and MCI stages: Results by Deep sequencing mass spec method.

|  | IP by Ab clone 2D3A8 | | | | |
|---|---|---|---|---|---|
|  | P1 | P2 | P3 | P4 | P5 |
| Stable Cognitive Normal | 0 | 0 | 0 | 0 | 0 |
| Stable Alzheimer's disease with dementia | 3 | 3 | 2 | 1 | 3 |
| Preclinical (Cognitive Normal to AD converters) | 3 | 3 | 0 | 3 | 0 |
| MCI Stable | 0 | 0 | 0 | 1 | 0 |
| Prodromal (MCI converted to Alzheimer's) | 3 | 3 | 1 | 0 | 0 |

N of transiction 1 can be interpreted as "possible negative", N of transiction = 2 is a possible; N of transictions = 0 is "negative" and N of transictions = 3 is positive.

Example 2. Validation of a p53 Conformational Human Plasma Biomarker Specific to Alzheimer's Disease at the Pre-Clinical and Prodromal Stages of the Disease Initial results from a longitudinal four-year study on clinical progression of cognitively normal subjects and people with mild cognitive impairment to probable AD measuring U-p53 signals measured by direct ELISA, shown very high predictive values for progression. Based on this finding, it was developed a highly accurate mass spectrometry method based on the identification of p53 peptides P1 and/or P2, for the diagnosis of Alzheimer's at the preclinical and prodromal stages of the disease and for the prognosis of cognitive decline. The maximum prognostic PPV for cognitive decline to Alzheimer's dementia was achieved in both subjects with MCI and asymptomatic. It is believed that both the diagnostic and prognostic performance of the p53 peptides, P1 and/or P2, is the highest that has been reported to date.

A specific mass spec method, which is the SRM (Selected Monitoring Reaction) method (by triple quadrupole mass spectrometer) was used to quantify both P1 and/or P2 in plasma samples from AD, asymptomatic, MCI subjects. By the triple quadrupole mass spectrometer which acts as essentially as a mass filter, it is possible to sequence the peptides by looking at the different transition peaks. Then, using a heavy labelled internal control for peptide 1 and 2, it is possible to quantitate those peptides with the maximum precision by Selected Monitoring Reaction (SRM) method.

Prognostic Performance

It was evaluated the prognostic power of the biomarker in enriching for patients who are PiB+ but also will exhibit cognitive decline in 18 months from MCI subjects and in 18-72 months for asymptomatic subjects at presentation. This was performed, in order to assess the value of the biomarker in significantly enriching for cognitive decline as an endpoint in disease modifying trials in asymptomatic and patients with MCI. It was examined the prognostic power of P1 and P2, using the future conversion of clinical presentation. Statistical parameters able to describe the prognostic power of P1 and P2 are below reported:

TABLE 3

Prognostic Power of Asymptomatic subjects to AD diagnosis

| | Sequence peptide 1 | Sequence Peptide 2 |
|---|---|---|
| Sensitivity | 72.2% | 89% |
| Specificity | 95.5% | 100% |
| PPV (positive predictive value) | 70.2% | 100% |
| NPV (negative predictive value) | 99.7% | 99.8% |
| AUC | 83% | 90.7% |
| P-value | 0.0022 | 0.0020 |

TABLE 4

Prognostic Power of MCI subjects to AD diagnosis

| | Sequence peptide 1 | Sequence Peptide 2 |
|---|---|---|
| Sensitivity | 95% | 100% |
| Specificity | 95% | 100% |
| PPV (positive predictive value) | 88.2% | 100% |
| NPV (negative predictive value) | 98% | 100% |
| AUC | 96.3% | 100% |
| P-value | 0.0082 | 0.4724 |

Conclusions

P1 and P2 can accurately enrich for patients that will exhibit cognitive decline from either an asymptomatic or MCI clinical presentation with very high specificity and sensitivity and thus enable the successful recruitment of patients for disease modifying drugs targeting the very early stages of the disease.

Example 3

Differential Diagnosis of Alzheimer's Disease from Other Forms of Dementia

An analysis was also performed to validate previous data on the specificity of the U-P53 biomarker in Alzheimer's dementia. Well characterized Alzheimer's patients which were amyloid positive and had Alzheimer's dementia were compared with patients with clinical presentations of other dementias such as FTD (frontal-temporal dementia), Parkinson's, Lewi's Body and vascular dementia.

Plasma samples from OD (FTD, Vascular, Parkinson's, Lewi's Body) were collected at disease stage, anyway in a differential diagnosis, it is possible to establish that above a certain cutoff both peptide sequences showed a high specificity and sensitivity toward AD compared to OD.

Furthermore, it has been observed that AUC of both peptides is greater than 90%, it shows the high correlation between biomarker concentration and the AD diagnosis.

There is in literature an unmet need in differential diagnosis in Alzheimer's dementia is between: a) advanced FTD and advanced AD b) advanced LBD and AD as those can mimic clinical presentation is some cases. Anything that can exclude either AD or the other dementia has clinical value, thus high sensitivity of either dementia is enough to bring value.

TABLE 5

Performance measures for p53 peptides P1 and P2 in differentiating Alzheimer's pathology from other Dementias in subjects with dementia.

| | Sequence peptide 1 | Sequence Peptide 2 |
|---|---|---|
| Sensitivity | 100% | 80% |
| Specificity | 85.7% | 85.7% |
| PPV (positive predictive value) | 87.5% | 84.8% |
| NPV (negative predictive value) | 100% | 81.1% |
| AUC | 94.3% | 90.7% |
| P-value | 0.0510 | 0.0171 |

REFERENCES

1. Stanga, S. et al., 2010. Unfolded p53 in the pathogenesis of Alzheimer's disease: Is HIPK2 the link? Aging, 2(9), pp. 545-554.
2. Lanni, C. et al., 2007. Unfolded p53: A potential biomarker for Alzheimer's disease. In Journal of Alzheimer's Disease. pp. 93-99.
3. Uberti, D. et al., 2008. Conformationally altered p53: a putative peripheral marker for Alzheimer's disease. Neuro-degenerative diseases, 5(3-4), pp. 209-11.
4. Lanni, C. et al., 2008. Conformationally altered p53: a novel Alzheimer's disease marker? Molecular psychiatry, 13(6), pp. 641-7.
5. Lanni, C., Racchi, M., et al., 2010. Unfolded p53 in blood as a predictive signature signature of the transition from mild cognitive impairment to Alzheimer's disease. Journal of Alzheimer's disease: JAD, 20(1), pp. 97-104.
6. Buizza, L. et al., 2012. Conformational altered p53 as an early marker of oxidative stress in Alzheimer's disease. PloS one, 7(1), p.e29789
7. Arce-Varas N, et al. Comparison of extracellular and intracellular blood compartments highlights redox alterations in Alzheimer's and Mild Cognitive Impairment patients. Current Alzheimer Research 2017; 14(1): 112-122.

8. Uberti, D. et al., 2006. Identification of a mutant-like conformation of p53 in fibroblasts from sporadic Alzheimer's disease patients. Neurobiology of aging, 27(9), pp. 1193-201.
9. Lanni, C., Nardinocchi, L., et al., 2010. Homeodomain interacting protein kinase 2: a target for Alzheimer's beta amyloid leading to misfolded p53 and inappropriate cell survival. PloS one, 5(4), p.e10171.
10. Lanni, C. et al., 2008. Pharmacogenetics and Pharmagenomics, Trends in Normal and Pathological Aging Studies: Focus on p53. Current Pharmaceutical Design, 14(26), pp. 2665-2671.

The invention claimed is:

1. An in vitro or ex vivo method for the diagnosis of Alzheimer's disease or prognosis of cognitive decline leading to dementia in a subject, the method comprising:

subjecting a biological sample comprising plasma from said subject to immunoprecipitation using an antibody specific for p53 protein to form an immunocomplex comprising p53 protein and said antibody, wherein said antibody specific for p53 protein comprises a heavy chain variable region comprising CDR1 (SEQ ID NO:10), CDR2 (SEQ ID NO: 11) and CDR3 (SEQ ID NO: 12) and a light chain variable region comprising CDR1 (SEQ ID NO:13), CDR2 (SEQ ID NO: 14) and CDR3 (SEQ ID NO: 15);

separating said p53 protein from said antibody to provide isolated p53 protein from said subject;

subjecting said isolated p53 protein to protease digestion to generate one or more peptides comprising one or both of peptides P1 and P2, said peptide P1 having (SEQ ID NO. 1 TEEENLR) and said peptide P2 having (SEQ ID NO. 2 TEEENLRK[GG]K), wherein said one or peptides are proteolytic products of said protease digestion;

isolating said one or more proteolytic products; and comparing an amount of each of said one or more proteolytic peptides in a reaction mixture to an amount of each of one or more respective control peptides, wherein a higher amount of said one or more proteolytic peptides relative to said one or more respective control peptides indicates Alzheimer's disease or cognitive decline leading to dementia in said subject.

2. The method of claim 1, wherein said cognitive decline is Mild Cognitive Impairment.

3. The method of claim 1, wherein said comparing is performed using mass spectrometry analysis.

4. The method of claim 3, wherein said mass spectrometry analysis comprises HPLC-mass spectrometry.

5. The method of claim 1, wherein said each said peptide control peptide is a labeled peptide.

6. The method of claim 5, wherein a said labeled control peptide is internal to said reaction mixture and is represented as a value comprising its concentration in said reaction mixture.

7. The method of claim 1, wherein said comparing is performed using Selected Reaction Monitoring (SRM).

8. The method of claim 6, wherein said comparing is performed using Selected Reaction Monitoring (SRM) and said SRM identifies and quantifies said one or more peptides comprised by said reaction mixture by comparing the same with said peptide control value.

9. The method of claim 1, wherein said biological sample is subjected to protein plasma depletion prior to said immunoprecipitation.

10. The method of claim 9, wherein said protein plasma depletion is accomplished by one or more of: HPLC, a chromatographic column, and/or chemical treatment of said biological sample.

11. The method of claim 1, wherein the method provides for the diagnosis of Alzheimer's disease in an asymptomatic subject or in a subject exhibiting mild cognitive impairment.

12. The method of claim 1, wherein the method provides for prognosis of cognitive decline in an asymptomatic subject or a subject exhibiting mild cognitive impairment.

13. The method of claim 11, wherein said prognosis is for cognitive decline leading to dementia.

14. The method of claim 13, wherein said prognosis is for said cognitive decline leading to said dementia leading to Alzheimer's disease.

15. The method of claim 1, wherein said comparing comprises quantifying said P1 peptide relative to a control peptide P1.

16. The method of claim 1, wherein said comparing comprises quantifying said peptide P2 relative to a control peptide P2.

17. The method of claim 1, wherein said antibody comprises a heavy chain variable region having SEQ ID NO: 8 and a light chain variable region having SEQ ID NO: 9.

18. The method of claim 1, wherein said antibody comprises a heavy chain having SEQ ID NO: 6 and a light chain having SEQ ID NO: 7.

* * * * *

UNITED STATES PATENT AND TRADEMARK OFFICE
CERTIFICATE OF CORRECTION

| | |
|---|---|
| PATENT NO. | : 11,650,215 B2 |
| APPLICATION NO. | : 17/113559 |
| DATED | : May 16, 2023 |
| INVENTOR(S) | : Maurizio Memo et al. |

It is certified that error appears in the above-identified patent and that said Letters Patent is hereby corrected as shown below:

In the Claims

At Column 20, Claim number 5, Line number 66, please delete "peptide".

Signed and Sealed this
Twenty-fifth Day of July, 2023

Katherine Kelly Vidal
*Director of the United States Patent and Trademark Office*